(12) United States Patent
Kroll et al.

(10) Patent No.: US 7,689,280 B1
(45) Date of Patent: Mar. 30, 2010

(54) AUTOMATIC SYSTEM FOR DETERMINING BI-VENTRICULAR PACING RESPONDERS

(75) Inventors: Mark W. Kroll, Orono, MN (US); Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 930 days.

(21) Appl. No.: 11/290,938

(22) Filed: Nov. 29, 2005

(51) Int. Cl.
    *A61N 1/08* (2006.01)
(52) U.S. Cl. .......................................... 607/9; 607/28
(58) Field of Classification Search ............... 607/9, 607/28
    See application file for complete search history.

(56) References Cited

U.S. PATENT DOCUMENTS

| 2003/0100925 | A1 | 5/2003 | Pape et al. ............... 607/17 |
| 2004/0015081 | A1 | 1/2004 | Kramer et al. ........... 600/439 |
| 2005/0182447 | A1* | 8/2005 | Schecter .................. 607/2 |

FOREIGN PATENT DOCUMENTS

WO  WO 2004/008955 A2  1/2004
WO  WO 2004/008955 A3  1/2004

\* cited by examiner

*Primary Examiner*—Mark W Bockelman
*Assistant Examiner*—Eric D. Bertram

(57) ABSTRACT

A method of predicting a patient's response to multi-chamber pacing by implanting at least three sensing electrodes, measuring across at least two different impedance vectors of the heart via the three electrodes to obtain at least two impedance signals, and evaluating the at least two impedance signals for indications of contractile dysynchrony. Contractile dysynchrony indicates that the patient is likely to have a positive response to multi-chamber pacing. Also an implantable cardiac stimulation device with an implantable housing, a stimulation pulse generator positioned within the housing, at least two implantable leads, and a controller communicating with the pulse generator to induce the generator to deliver therapeutic stimulation to a patient's heart. The leads are arranged to measure a physiological parameter along at least two different spatial orientations. The controller evaluates relative timing of the physiological parameters along the different orientations for indications of contractile synchrony of the patient's heart.

20 Claims, 7 Drawing Sheets

| Comparisons of Baseline Characteristics of Responders and Nonresonders | | | |
|---|---|---|---|
| | Responders (n = 12) | Nonresponders (n = 8) | p Value |
| ECG parameters | | | |
| Heart rate (beats/min) | 68 ± 15 | 76 ± 12 | NS |
| PQ interval (ms) | 213 ± 27 | 186 ± 23 | <0.05 |
| QRS duration (ms) | 173 ± 18 | 164 ± 12 | NS |
| Echocardiographic parameters | | | |
| SPWMD (ms) | 246 ± 68 | 110 ± 55 | <0.001 |
| LVEMD (ms) | 176 ± 40 | 163 ± 55 | NS |
| IVD (ms) | 59 ± 19 | 73 ± 21 | NS |
| LVEDVI (ml/m$^2$) | 162 ± 65 | 132 ± 23 | NS |
| LVESVI (ml/m$^2$) | 125 ± 52 | 103 ± 19 | NS |
| LVEF (%) | 24 ± 4 | 23 ± 5 | NS |
| MR$_d$ (ms) | 559 ± 63 | 561 ± 58 | NS |
| MR$_a$ (mm$^2$) | 9.8 ± 1.8 | 10.2 ± 5.5 | NS |

FIG. 3

AUTOMATIC SYSTEM FOR DETERMINING BI-VENTRICULAR PACING RESPONDERS

FIELD OF THE INVENTION

The invention relates to the field of implantable medical devices and more particularly to systems for automatically determining patients likely to respond to bi-ventricular pacing and/or for improving the delivery of such therapy.

BACKGROUND OF THE INVENTION

A wide variety of health ailments involving cardiac arrhythmias can be effectively treated with implantable cardiac stimulation devices. The range of arrhythmias includes various bradycardia conditions, which can be treated with cardiac pacing and tachycardia conditions, which can be treated with anti-tachycardia pacers and/or implantable cardioverter/defibrillators as appropriate to the patient's condition. The implantable devices used range in complexity and modes of therapy delivery, such as the particular chambers of the heart which receive therapeutic stimulation, depending on clinical evaluations of the individual needs of the patient. Thus, an implantable cardiac stimulation device and corresponding implantable sensing/stimulation lead(s) are configured and programmed for the individual needs of each patient and their arrhythmic condition.

Cardiac arrhythmia conditions also frequently occur coincident with a congestive heart failure (CHF) condition. CHF refers broadly to a variety of health ailments characterized by a reduction in the mechanical ability of the heart to pump an appropriate supply of blood. CHF can encompass an enlargement of the heart muscle, a degradation of the contractile properties of the heart, and/or a reduction in the synchrony in the cardiac contractions. CHF can also correspond to damage to or deterioration of heart valves and other structural conditions which reduce the cardiac output.

Multi-chamber pacing can offer significant benefits to certain arrhythmic patients and frequently such patients also suffer from some degree of CHF. Bi-ventricular pacing is one particular variation of multi-chamber pacing that refers to pacing both the right and left ventricles as indicated. By providing paced control of both ventricles, bi-ventricular pacing can help restore synchrony between the ventricles and increase the overall pumping efficiency of the heart. While this treatment can be quite effective for certain patients, including many CHF patients, some patients do not respond well to bi-ventricular pacing.

Multi-chamber pacing is one of the more complicated therapies available via implantable cardiac stimulation devices. In the particular example of bi-ventricular pacing, as the left ventricle (LV) provides the most energetic contractions of the heart chambers and placing foreign objects inside the LV presents serious risks, implanting stimulation leads into effective contact with the left ventricle is a challenging procedure both for the designers of the implantable device and the physician performing the implantation. Thus, bi-ventricular pacing, while offering significant benefits to certain patients, is also relatively expensive to implement and involves a more complicated and potentially more risky implantation procedure than other implantable device configurations. As many potential implantees are covered by either private or governmental health insurance, it will be appreciated that this more complex and expensive therapy is often reserved for patients for whom a clear potential benefit can be demonstrated.

Thus, it will be appreciated that being able to readily identify and characterize either the onset of a condition which is likely responsive to multi-chamber pacing as well as the ongoing severity of the condition can provide a valuable diagnostic tool to a clinician to provide more effective therapy. A variety of examinations and observations are known which can be utilized by a clinician to evaluate the existence or progression of a CHF condition and to identify indications for multi-chamber devices. A physical examination and interview of the patient can reveal, for example, edema and/or weight gain caused by fluid accumulation, which is a frequent symptom of CHF. Shortness of breath is also a common symptom of CHF and an interview of the patient and examination can reveal the severity of and conditions under which the shortness of breath occurs. An examination can also reveal a third heart sound, frequently referred to as S3, as well as a sound of fluid in the lungs during inspiration (rales), either of which are common symptoms of CHF. A clinician may also observe enlargement of the jugular vein in the neck region (jugular venous distention), enlargement of the liver (hepatomegaly), and this may be coupled with a hepatojugular reflex wherein an enlarged liver which is subjected to manual pressure forces more blood into the jugular veins, causing them to become even more enlarged.

Several diagnostic tests are also useful in diagnosing CHF, including chest x-rays which can reveal pulmonary edema, an enlarged heart, and pleural effusion. Electrocardiograms (EKG/ECGs) are also useful for their ability to detect the presence of a heart attack, cardiac ischemia, abnormal heart rhythms, and/or an enlarged heart. Echocardiograms are another useful diagnostic tool which can determine the amount of blood ejected from the heart with each heartbeat, and more particularly, the proportion of blood ejected which is typically referred to as the ejection fraction. Ejection fraction is frequently depressed in likely responders to multi-chamber pacing. Echocardiograms can also diagnose particular causes of CHF, including heart valve abnormalities, pericardial abnormalities, congenital heart disease, and/or an enlarged heart. Echocardiograms can also show if the contraction of the heart itself is abnormal, such as in wall motion abnormalities, which lead to contractile dysynchrony, another indicator for multi-chamber pacing.

While these clinical observations and diagnostic tests offer valuable information for diagnosing a patient's condition, they suffer from the disadvantage of requiring the direct intervention of a highly trained clinician. The aforementioned patient observations require the training and judgment of a skilled clinician to accurately diagnose the patient observations. The aforementioned diagnostic tests, in addition to requiring the services of a skilled clinician, also typically require that the tests take place in a clinical setting. Diagnostic equipment, such as chest x-ray and echocardiogram machines, are large, complex, and relatively expensive pieces of equipment which are neither portable nor economical for the dedicated service of a single patient. Thus, the aforementioned observations and diagnostic tests are not suitable for frequent ongoing diagnosis of a patient's condition but rather are more suitable to serve relatively large number of patients at scheduled clinical appointments.

SUMMARY OF THE INVENTION

Thus, there is a need for systems and methods for evaluating a patient's condition on an ongoing basis without requiring the immediate attention of a skilled clinician and complex diagnostic equipment, such as in a clinical setting. There is a further need for systems and methods of establishing the onset of a condition that would likely be responsive to multi-chamber pacing so that the patient can be referred for possible implantation of a multi-chamber pacing system. There is also a need for updating pacing parameters of multi-chamber devices for changes in patients already provided with a multi-chamber pacing system.

Embodiments of the invention employ an implantable device to separately measure multiple impedance vectors across regions of a patient's heart to evaluate the degree of synchrony with which the multiple chambers of the heart are pumping. Reduced contractile synchrony is associated with more serious CHF and is also an indicator for likely responsiveness to bi-ventricular pacing. An implantable device that is not presently configured for bi-ventricular pacing can evaluate the contractile synchrony of the heart, including with respect to the left ventricle, and can automatically determine onset of conditions indicating treatment with a bi-ventricular pacer, according to embodiments of the invention. Thus, according to certain embodiments, a relatively simpler device implanted with a simpler implantation procedure can automatically determine that an implantee is likely to benefit from a device having expanded treatment capability, e.g. a bi-ventricular pacer.

Embodiments of the invention also include methods of evaluating the relative timing of corresponding cardiac events in measurements made along different spatial orientations for determination of the synchrony of the heart chambers. The evaluation can comprise calculating a correlation between multiple signals as well as determination/comparison of phase differences between the multiple signals. Reduced correlation or similarly more pronounced phase differences are interpreted as corresponding to reduced contractile synchrony and positive indicators for a more severe CHF condition and/or likely responsiveness to bi-ventricular pacing. Increased correlation/reduced phase differences are interpreted as corresponding to increased synchrony. This can be utilized to adjust device parameters for patients already provided with a bi-ventricular pacing capable device.

Thus, one embodiment is a method of predicting a patient's response to multi-chamber pacing comprising implanting at least three sensing electrodes, measuring across at least two different impedance vectors of a patient's heart via the at least three electrodes so as to obtain at least two impedance signals, and evaluating the at least two impedance signals for indications of contractile dysynchrony in the heart and wherein indications of contractile dysynchrony comprise positive indicators for the patient's response to multi-chamber pacing.

Another embodiment is an implantable cardiac stimulation device comprising an implantable housing, a stimulation pulse generator positioned within the housing, at least two implantable leads, and a controller in communication with the pulse generator so as to induce the generator to deliver therapeutic stimulation to a patient's heart via at least one of the leads and wherein the leads are arranged to measure a physiological parameter along at least two different spatial orientations and wherein the controller evaluates the relative timing of the physiological parameters along the different orientations for indications of contractile synchrony of the patient's heart.

Yet another embodiment is a method of evaluating a patient's condition comprising measuring at least two different signals across a patient's heart between at least three different spatial locations, correlating the at least two signals, comparing the correlation of the at least two signals to a threshold value, and, upon a determination from the comparing that the correlation is less than the threshold value, setting an alert flag indicating a change in the patient's condition.

A further embodiment is an implantable cardiac stimulation device, wherein the device is of a first configuration and automatically evaluates an implantee's condition and, upon determination that the implantee is likely to respond to bi-ventricular pacing, provides a signal indicating elective replacement of the device of the first configuration with a device of a second configuration to provide bi-ventricular pacing. These and other objects and advantages of the invention will become more apparent from the following description taken in conjunction with the accompanying drawings.

BRIEF DESCRIPTION OF THE DRAWINGS

FIG. 3 is a table indicating various observed parameters of a group of patients including responders and non-responders to bi-ventricular pacing;

DETAILED DESCRIPTION OF THE PREFERRED EMBODIMENT

Reference will now be made to the drawings wherein like numerals refer to like parts throughout. The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
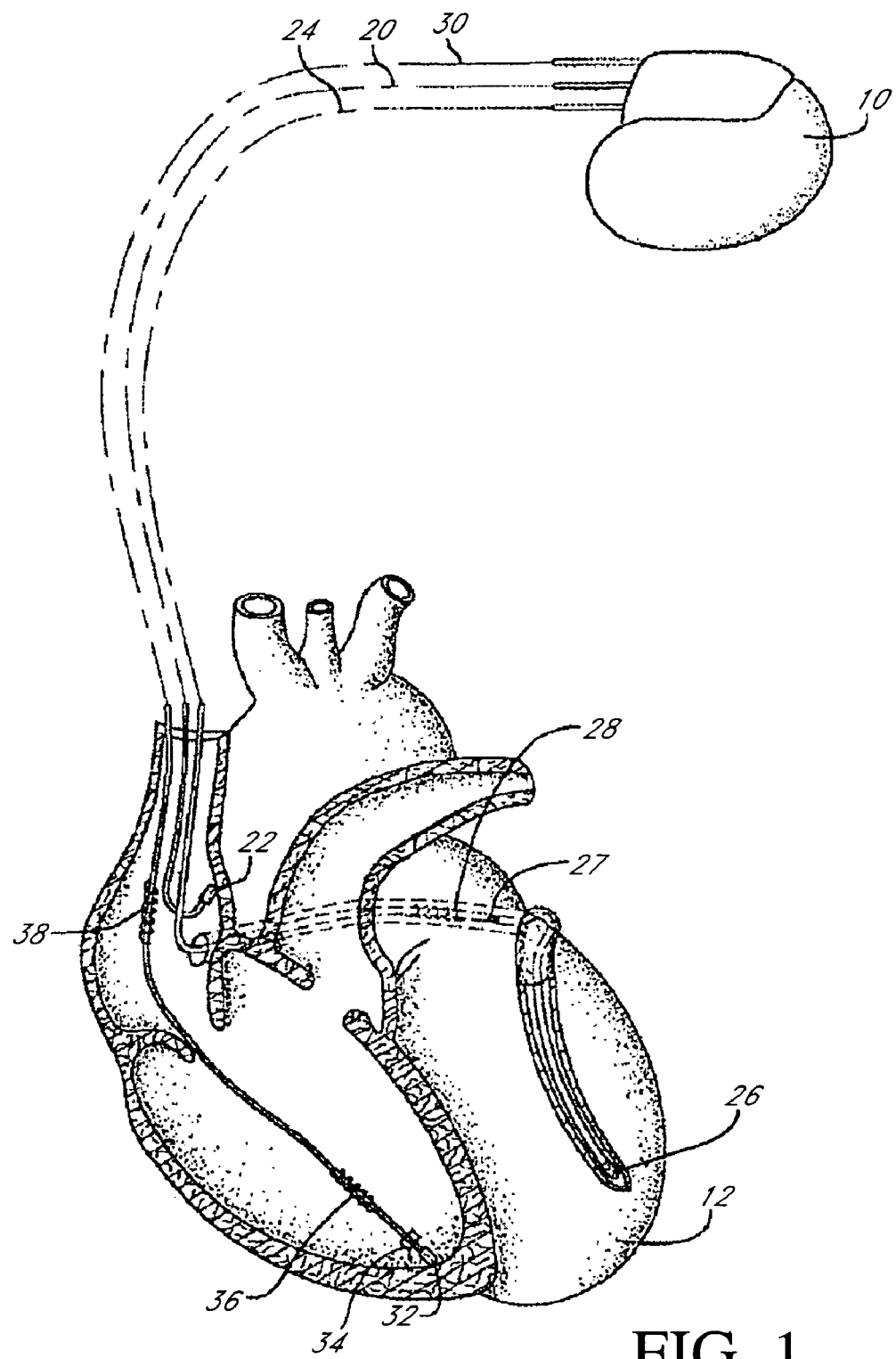
FIG. 1 is a simplified diagram illustrating an implantable stimulation device in electrical communication with at least three leads implanted into a patient's heart for delivering multi-chamber stimulation and shock therapy.

In one embodiment, as shown in FIG. 1, a device 10 comprising an implantable cardiac stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
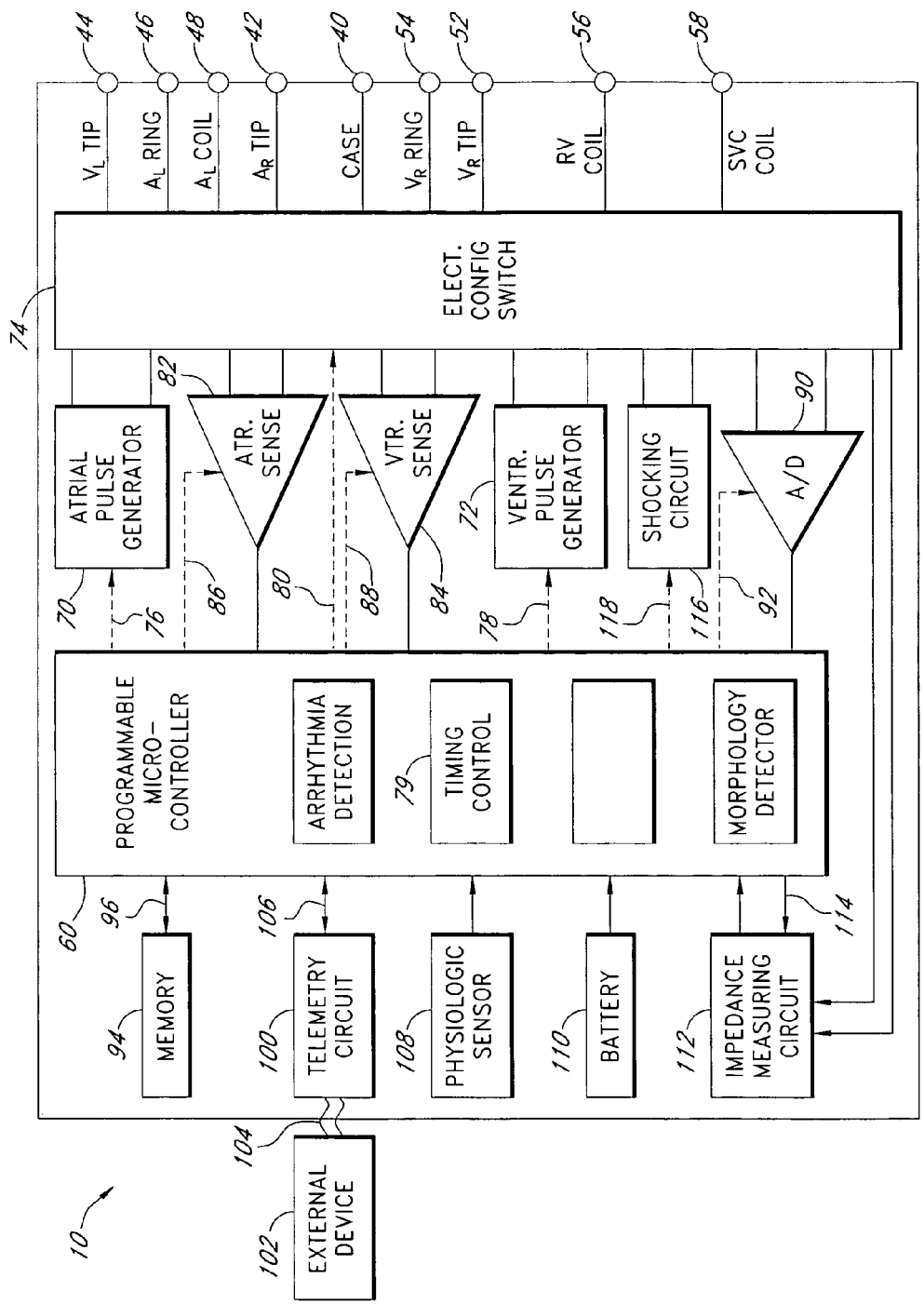
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art. In this embodiment, the switch 74 also supports simultaneous high resolution impedance measurements, such as between the case or housing 40, the right atrial electrode 22, and right ventricular electrodes 32, 34 as described in greater detail below.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independently of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation) are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows IEGMs and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time and then be capable of providing high-current pulses (for capacitor charging) when the patient requires a shock pulse. The battery 110 must also have a predictable discharge characteristic so that elective replacement time can be detected. Accordingly, embodiments of the device 10 including shocking capability preferably employ lithium/silver vanadium oxide batteries. For embodiments of the device 10 not including shocking capability, the battery 110 will preferably be lithium iodide or carbon monoflouride or a hybrid of the two.

As further shown in FIG. 2, the device 10 is shown as having an impedance measuring circuit 112 which is enabled by the microcontroller 60 via a control signal 114.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As previously noted, clinically based diagnostic equipment can be used to assist in the evaluation of patients' likely responsiveness to multi-chamber pacing therapy. FIG. 3 illustrates in greater detail examples of certain parameters revealed by ECG and echocardiogram diagnostics. These parameters are separated into a group of patients who exhibited positive response to bi-ventricular pacing (n=12) and those who did not (n=8). For example, both responders and non-responders exhibited an elongated QRS duration (as compared to a normal, healthy duration), however there was not a statistically significant difference between the two groups. However, the delay between the septal and posterior wall motion (SPWMD) did exhibit a marked and statistically significant (p<0.001) difference between the two groups with responders having a mean SPWMD of 246±68 ms as compared to 110±55 ms for the non-responsive group or a difference in the mean of over a factor of two. Thus, an elongated SPWMD period can be utilized as an indicator for likely responsiveness to bi-ventricular pacing. Embodiments of the invention are directed towards automatically determining a patient's likely responsiveness to multi-chamber pacing with reduced need for clinically based diagnostic equipment.

Figure 4:
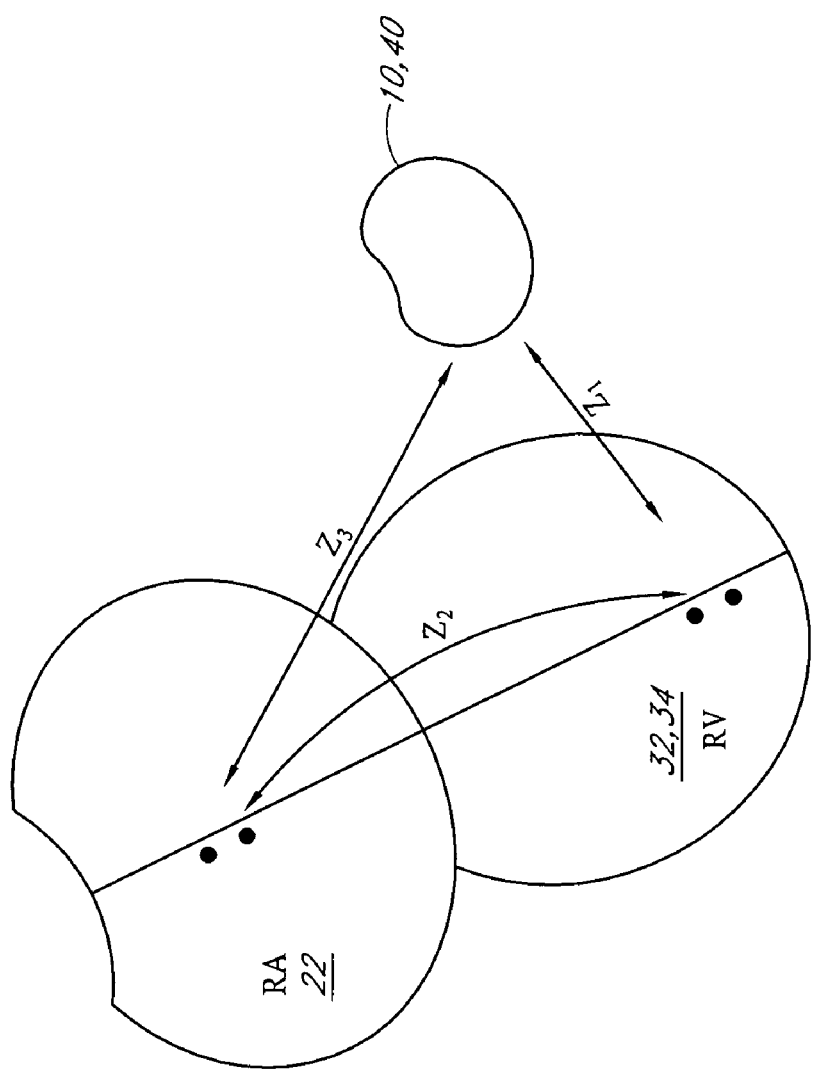
FIG. 4 is a schematic diagram illustrating one embodiment of multiple impedance vectors among chambers of a patient's heart and an implantable medical device.

FIG. 4 is a schematic illustration of a plurality of vectors defined when the device 10 is implanted in the patient with the vectors defined between regions of the heart 12 and the device 10. Is this particular embodiment, a first impedance vector $Z_1$ is defined between the device 10 and the right ventricle of the patient, for example, as defined by the circuit nodes of the right ventricular electrodes 32, 34. A second impedance vector $Z_2$ is defined in this embodiment between the right chambers of the patient's heart 12, in this particular embodiment between the circuit nodes defined by the atrial tip electrode 22 and the right ventricular tip electrode 32 or right ventricular ring electrode 34. A third impedance vector $Z_3$ is defined between the patient's right atrium, such as defined by the right atrial tip electrode 22 and the device 10. As previously mentioned, the can or housing 40 of the device 10 can act as an electrode, such as in the determination of the first impedance vector $Z_1$ and third impedance vector $Z_3$ of these embodiments.

The multiple vectors, such as the impedance vectors $Z_1$ through $Z_3$, comprise multiple independent pathways which are arranged along different spatial orientations across which the characteristics of the patient's heart 12 can be measured via the device 10 as implanted within the patient. The multiple impedance vectors $Z_1$, $Z_2$, $Z_3$ will exhibit time-varying characteristics throughout the cyclical depolarizations and re-polarizations of the cardiac tissue. The multiple impedance vectors are preferably selected to provide information indicative of the characteristics of various wall segments of the heart 12. In this embodiment, the arrangements of the first, second, and third impedance vectors $Z_1$, $Z_2$, $Z_3$ measure impedance characteristics that are indicative of the left ventricular contractions and are particularly arranged to be able to detect timing differences in the contractions of the various wall segments of the patient's heart 12. This can be utilized to provide indications of contractile dysynchrony to automatically determine the likely responsiveness of a patient to bi-ventricular pacing. It will be appreciated that the multiple impedance vectors illustrated schematically in FIG. 4 can develop information indicative of the left ventricular activity, however do not require direct sensing of the left ventricle chamber, such as by implanted electrodes.

In one embodiment, the system described in FIG. 4 is incorporated in a conventional dual chamber pacemaker or defibrillator. Such a device could monitor, over time, the patient's heart condition, and upon detection of heart failure progression based on the impedance values from the plural vectors, the device could generate an elective replacement signal recommending an upgrade to a biventricular device. The elective replacement signal could be a patient notification signal, could be telemetered to a programmer at a follow-up session with a physician, or could be telemetered to a remote location via a transtelephonic system or over a computer network-based remote monitoring system.

In other embodiments, the multiple vectors $Z_1$, $Z_2$, $Z_3$ are developed from a configuration of device 10 that already includes multi-chamber sensing/stimulation characteristics and does provide direct sensing of the left ventricle. Information gathered related to contractile synchrony can be utilized to adjust programmed operational parameters of the device 10 to improve delivery of therapy, such as of bi-ventricular pacing, to the patient. In one particular embodiment, a patient is provided with a device 10 configured and programmed to provide cardiac resynchronization therapy (CRT). Evaluation of the multiple vectors can reveal that the patient is exhibiting an increased degree of contractile synchrony and the device 10 can be reprogrammed with different operational parameters in accordance with their current condition. In certain embodiments, the device 10 can perform such programming automatically.

In yet other embodiments, the vectors $Z_1$, $Z_2$, $Z_3$ correspond to direct measurements of motion of various wall segments of the heart 12. In this embodiment, a plurality of the physiologic sensors 108 comprising accelerometers are arranged to directly measure the movement of heart tissue and more particularly to independently measure the movement of wall portions. Thus, each sensor 108 can independently measure an associated heart chamber wall and the vectors $Z_1$, $Z_2$, $Z_3$ provide independent signals indicative of this movement. In various embodiments, the vectors $Z_1$, $Z_2$, $Z_3$ can be analyzed with respect to each other as well as with electrical measurements, for example an intracardiac electrogram (IEGM), to evaluate the heart's synchrony as described in greater detail below.

Figure 5:
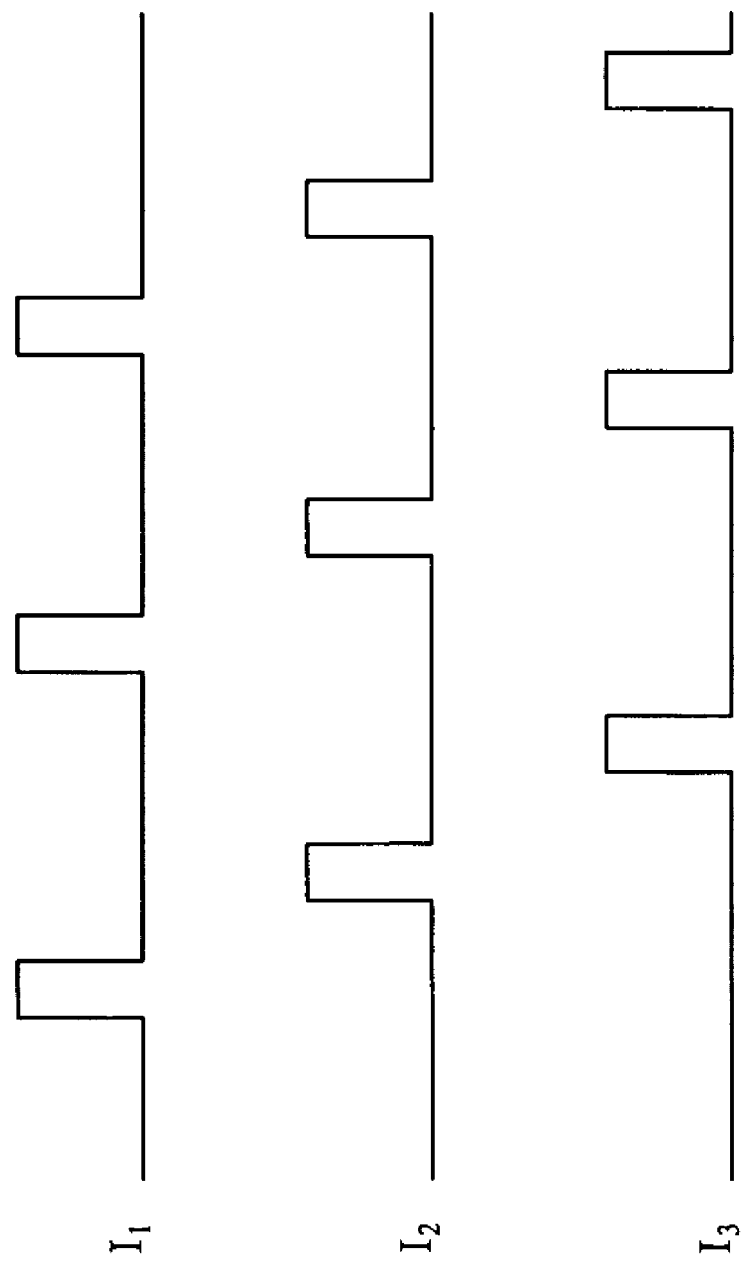
FIG. 5 illustrates waveforms corresponding to one embodiment of relative timing of application of separate test current pulses for evaluation of multiple impedance vectors.

FIG. 5 illustrates an exemplary waveform of corresponding test current pulse trains which are used in certain embodiments to determine the multiple vectors comprising the impedance vectors $Z_1$, $Z_2$, $Z_3$. More particularly, FIG. 5 illustrates a particular embodiment comprising a first, a second, and a third current pulse trains $I_1$, $I_2$, $I_3$ corresponding respectively to the determinations of the first, second, and third impedance vectors $Z_1$, $Z_2$, $Z_3$. This particular embodiment reduces current and signal mixing along the various vectors illustrated schematically in FIG. 4 by pulsing or otherwise providing separate test current independently in a non-overlapping manner.

Thus, in the particular embodiment illustrated by the waveforms of FIG. 5, the test current pulses provided by the first, second, and third current pulse trains $I_1$, $I_2$, $I_3$ are separated in time from each other to reduce current and signal mixing to facilitate more accurate determination of the first, second, and third impedance vectors $Z_1$, $Z_2$, $Z_3$. This separation of the current vectors is an important feature of aspects of the invention. If the impedances were to be measured by simultaneous currents, the impedance measurements would be mixed and blurred. Thus one preferred embodiment is the "time multiplexing" as described above.

However, another useful embodiment would use a different code sequence along each vector. The voltage signals would then be decoded to separate out accurate independent impedance vectors. This approach can be referred to as code division multiplexing (CDM). Yet another useful embodiment is to use different frequencies for each vector. This is referred to as "frequency multiplexing." Each of these embodiments provides the ability to more clearly distinguish each separate vector measurement and avoid blurring or mixing of the measurements.

In one particular embodiment, the current pulse trains $I_1$, $I_2$, $I_3$ are provided by a rotating three-phase current source that is sequentially connected to two of the three electrodes at a time, e.g., between the right atrial tip electrode 22, the housing 40, and the right ventricular tip electrode 32 or ring electrode 34. Each pulse of the current pulse trains $I_1$, $I_2$, $I_3$ is approximately 0.1 to 1 mA in amplitude, of approximately 15-45 μs width/duration and provided at a sampling rate of approximately 64-512 Hz. The current pulse trains $I_1$, $I_2$, $I_3$ are preferably delivered when the patient is resting as the measured values of the impedance vectors $I_1$, $I_2$, $I_3$ are relatively sensitive to the patient's posture. It is desirable to reduce influence in the measurement such as from changes in the patient's posture and muscular activity. In embodiments wherein the vectors $Z_1$, $Z_2$, $Z_3$ comprise motion vectors, measurement of the vectors is similarly preferably performed when the patient is resting to reduce the influence of muscular activity and posture changes on the measurement of the vectors. Various methodologies and algorithms for determining a patient's rest status will be well understood by one of ordinary skill.

Figure 6:
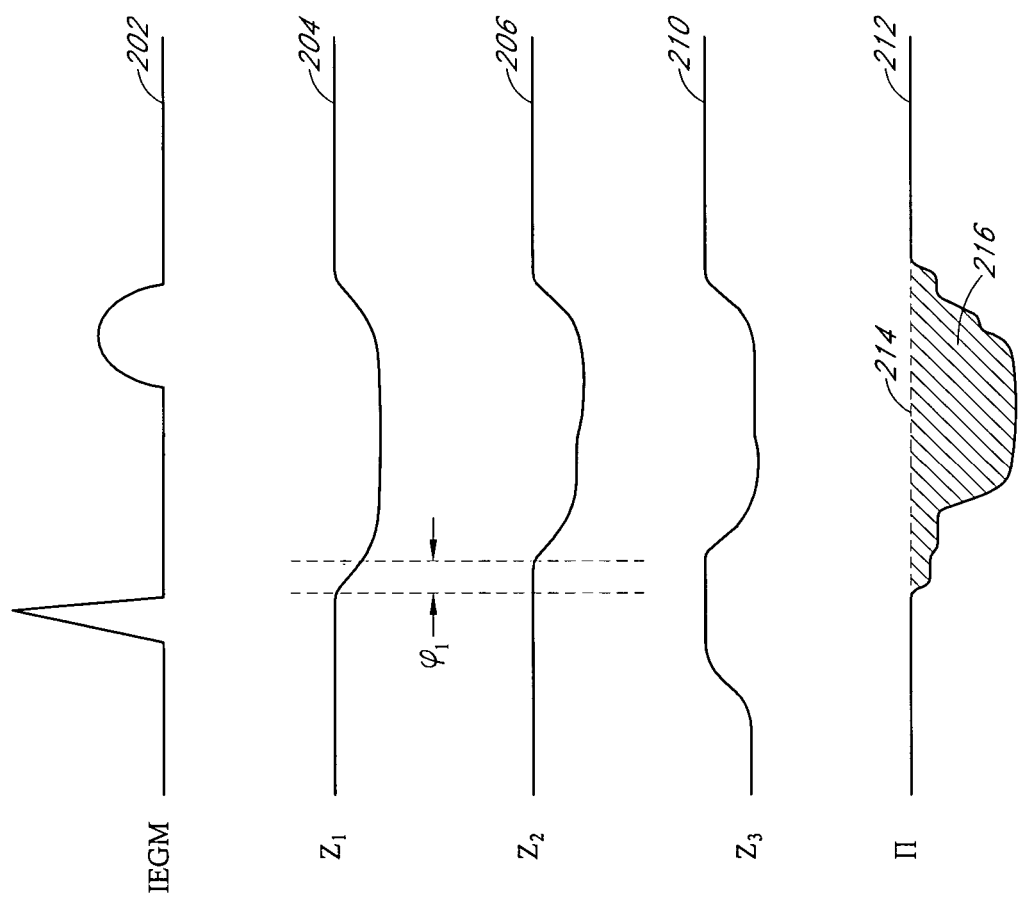
FIG. 6 illustrates simplified waveforms of one embodiment of measurement of multiple impedance and voltage characteristics of the patient's heart as well as one embodiment of a calculated waveform based upon the measurement.

FIG. 6 illustrates multiple simplified waveforms corresponding to time-varying parameters measured and/or calculated by one embodiment of the device 10. More particularly, FIG. 6 illustrates an electrocardiogram or intracardiac electrogram (IEGM) 202 which is indicative of the time-varying electrical activity of the heart 12 corresponding to the depolarizations and re-polarizations of the patient's/implantee's cardiac cycle. The waveform 204 illustrates the time-varying characteristics of the first vector $Z_1$ corresponding to the associated heart wall(s) activity. And, as can be seen by a comparison between the waveforms 202 and 204, the first vector $Z_1$ shows a change corresponding with the contraction beginning near the end of the QRS complex of the EKG waveform 202 and ending near the end of the T-wave. This contraction period is generally referred to as the "systolic" period.

The waveform 206 corresponds to the time-varying characteristics of the second vector $Z_2$ and, as can be seen, this signal exhibits a similar change between the end of the QRS complex and the baseline near the end of the T-wave. FIG. 6 also illustrates the waveform 210 corresponding to the time-varying characteristics of the third vector $Z_3$. The waveforms 204, 206 corresponding to the first and second vectors $Z_1$, $Z_2$ are similar in morphology, however, the first vector $Z_2$ as illustrated by the waveform 206 shows in its early stages the influence of the left atrial contraction and its influence upon the third vector $Z_3$. It can also be seen that, for example, between the waveforms 204, 206 of the signals $Z_1$ and $Z_2$ respectively, that corresponding cardiac events are not precisely synchronous and that, for example, a first phase shift $\phi_1$ exists between the different vectored measurements at the start of the systolic period. These phase shifts can also be evaluated to quantify a degree of contractile synchrony as will be described in greater detail below.

FIG. 6 also illustrates one embodiment of a calculated indicator 212 which also varies over time and is indicated in the figure by the designator ⊓. In one embodiment, the calculated indicator 212 comprises the point-by-point product of the three vectors $Z_1$, $Z_2$, $Z_3$ over time $\sqcap(t)=Z_1(t) \times Z_2(t) \times Z_3(t)$. In one particular implementation, the analog-to-digital (A/D) data acquisition system 90 provides discrete amplitude values for each of the vectors $Z_1$, $Z_2$, $Z_3$ over time to the microprocessor 60 which then performs a continuous multiplication operation of the amplitude values to obtain the values of the calculated indicator 212. In another embodiment, the calculated indicator 212 comprises a sum of the vectors $Z_1$, $Z_2$, $Z_3$. In this embodiment, the summation can similarly occur via processing by the micro-controller 60 of signals corresponding to the vectors $Z_1$, $Z_2$, $Z_3$ provided via the analog-to-digital (A/D) data acquisition system 90. The summation can also occur in a hardware implementation, such as via an operational amplifier (Op Amp) summer circuit.

In certain embodiments wherein the calculated indicator 212 comprises a product of the vectors $Z_1$, $Z_2$, $Z_3$, a baseline 214 is defined for the calculated indicator 212 and in this embodiment is defined as equal to zero such that the product ⊓ or calculated indicator 212 outside of the systolic period will be essentially zero. It will be appreciated that the ⊓signal has relatively low magnitude non-zero values at the beginning and at the end of a cycle due to the timing differences in the contraction signal between the three vectors $Z_1$, $Z_2$, $Z_3$ and the absence of a consistent zero value base signal among the vectors $Z_1$, $Z_2$, $Z_3$ (for example due to noise) which would inherently distort the product. Thus, the ⊓signal is normalized or zeroed in this embodiment for the amplitudes of the constituent vector signals $Z_1$, $Z_2$, $Z_3$ and appropriately corrected by the baseline 214.

An area under the curve of the ⊓signal 216 is calculated which then corresponds to the degree of correlation between the three vector signals $Z_1$, $Z_2$, $Z_3$. E.g., if the three vector signals $Z_1$, $Z_2$, $Z_3$ are substantially aligned in time exhibiting a relatively large degree of synchrony, a relatively large area 216 will be defined under the ⊓curve. In contrast, the area under the ⊓curve 216 will be comparatively reduced as the three vector signals $Z_1$, $Z_2$, $Z_3$ become more desynchronized or offset from each other in time, e.g. have an extended phase shift with respect to each other. Similarly to the generation of the calculated indicator 212, the area 216 can be determined by software based processing via the micro-controller 60 as well as in a hardware based manner, such as via an Op Amp integrator circuit depending on the particular implementation. Of course in other embodiments, a correlation or other measure of correspondence between any two or more measurements, such as a peak to peak delay or changing coherence, can be used as indicators of contractile dysynchrony.

Thus, as can be seen by comparing the waveforms illustrated in FIG. 6, the calculated indicator 212 corresponding in this particular embodiment to the product ⊓of the three first vectors $Z_1$, $Z_2$, $Z_3$ after baseline correction has a zero value where one or more of the vectors $Z_1$, $Z_2$, $Z_3$ has a zero value and reaches a peak when the three vectors $Z_1$, $Z_2$, $Z_3$ have their highest total product. Thus, perfect alignment between the three vectors $Z_1$, $Z_2$, $Z_3$ would result in a maximum area 216 for this embodiment of the calculated indicator 212 (such as illustrated by the ⊓waveform) and this would correspond to a normalized correlation of 1.0. Similarly, complete dysynchronization or complete lack of overlap among the first, second, and third vectors $Z_1$, $Z_2$, $Z_3$ would result in substantially zero area under the product ⊓curve which would correspond to a normalized correlation among the three vector signals $Z_1$, $Z_2$, $Z_3$ of zero. In certain embodiments, the normalization of the area 216 under the calculated indicator 212 curve to a normalized value between one and zero simplifies evaluation of the area 216, such as via comparison to one or more thresholds.

Higher normalized area under the product ⊓curve is indicative of greater synchronization of the heart 12 contractions as is exhibited by a normal healthy heart. In contrast, a reduced correlation or normalized area under the product ⊓curve is indicative of an increased dysynchronization (or phase delay/shift between various wall motions), such as may be due to wall motion abnormalities of the patient's heart 12. Thus, an indication of reduced correlation, e.g., increased dysynchronization in the heart 12 activity, can be evaluated and utilized as a diagnostic indicator for patients likely to benefit from bi-ventricular pacing treatment. Similarly, phase shifts, for example the phase shift $\phi hd\ 1$ can be evaluated where a reduced phase shift is indicative of desirable synchronization and extended phase shifts or significantly varying phase shifts among different wall segments is indicative of contractile dysynchrony.

Figure 7:
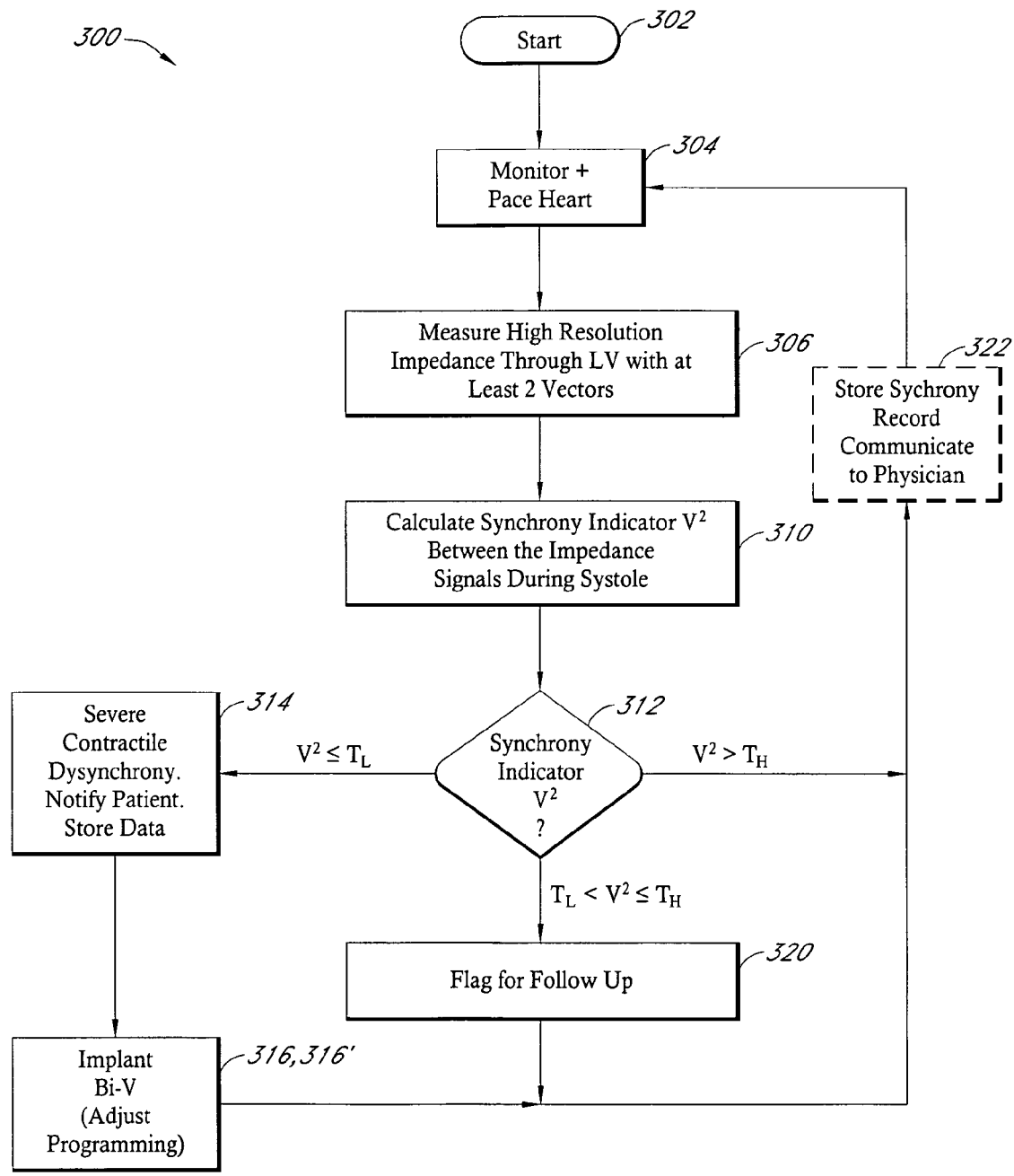
FIG. 7 is a flow chart of one embodiment of a method of automatically evaluating a patient's health status via an implantable device.

FIG. 7 is a flow chart of one embodiment of a system and method 300 for automatically determining likely responders to bi-ventricular pacing and/or evaluating a patient's condition based at least in part on evaluating contractile synchrony. In certain embodiments, the system and method 300 also include reprogramming a device 10 based at least in part on the evaluation of the patient's condition. Beginning from a start state 302, the method 300 includes a state 304 wherein the heart 12 is monitored and paced as indicated in an otherwise conventional fashion based on the particular configuration and programming of the device 10. As previously noted, in certain embodiments the device 10 is already configured for bi-ventricular pacing and in other embodiments, the method 300 determines the likelihood of the patient's responsiveness for bi-ventricular pacing.

The method 300 includes a measurement state 306 wherein measurements are made to determine motion of multiple walls of the heart 12. In one embodiment, high resolution impedance measurements are made through the left ventricle with at least two independent impedance vectors such as two or more of the previously described first, second, and third impedance vectors $Z_1$, $Z_2$, $Z_3$. In this embodiment, this is done with the independent test current pulses as illustrated by FIG. 5. In other embodiments, independent heart wall motion measurements are made as previously described to obtain the vectors $Z_1$, $Z_2$, $Z_3$.

The method 300 then proceeds to a calculation state 310 wherein a synchrony indicator $V^2$ is calculated among the two or more vectored signals during systole of the heart 12. In one embodiment, the synchrony indicator $V^2$ comprises the normalized correlation between the two or more vectors $Z_1$, $Z_2$, $Z_3$ as previously described. In other embodiments the synchrony indicator $V^2$ comprises phase shifts/timing delays such as between multiple vectors for corresponding contraction events as well as among separate contraction events of a single cardiac cycle in the corresponding multiple impedance vectors. Contraction events and contractile synchrony/dysynchrony as used herein refers to all or selected subsets of observable activity throughout the cyclical depolarization/repolarization of all of the heart chambers. Below, is given an exemplary formula for the synchrony indicator. If $Z_1=Z_2$ identically, then the formula would clearly give $V^2=1$ for the result. Hence, the closer the number to 1, the better the synchronization.

$$V^2 = \frac{\left[\int Z_1 Z_2 dt\right]}{2\sqrt{\int Z_1^2 dt \int Z_2^2 dt}}$$

Here is a similar formula for three vectors $$V^2 = \frac{\left[\int Z_1 Z_2 Z_3 dt\right]}{3\sqrt{\int Z_1^3 dt \int Z_2^3 dt \int Z_3^3 dt}}$$

Once the synchrony $V^2$ is calculated, a decision or comparison state 312 follows wherein the calculated synchrony indicator $V^2$ is compared to threshold values for indications of likely responsiveness to bi-ventricular pacing based on the degree of synchrony between the two or more vectors. In one embodiment, the synchrony indicator $V^2$ is compared to an upper threshold $T_H$ and a lower threshold $T_L$ and in one particular embodiment the upper threshold $T_H$ is equal to 0.9 and the lower threshold $T_L$ is equal to 0.8. In this particular embodiment, if the synchrony indicator $V^2$ is greater than the upper threshold $T_H$, the method 300 determines that the patient is exhibiting a desired level of synchrony as determined by measurements across the left ventricle. The method would return to the monitoring and pacing of state 304, as well as the further measurements and calculations of state 306 and 310 followed by the decision or comparison state of 312 for possible subsequent indications of a change in the synchrony of the patient's heart 12. This repetition and reevaluation can proceed continuously, periodically, e.g., hourly, daily, weekly, etc., and/or on a demand basis, such as via a command received via the telemetric link 104 depending upon the particular embodiment and application of the device 10 and method 300.

If the comparison or decision of state 312 indicates that the synchrony indicator is less than or equal to the lower threshold $T_L$, the method 300 and device 10 conclude in a state 314 that a condition of relatively severe contractile dysynchrony has been detected and would proceed to notify the patient. The notification of state 314 can occur via an audible tone, a stimulation signal delivered to the patient so as to be tactilely noticed and/or a telemetered signal provided to an external device 102 to provide the notification as well a wide variety of other mechanisms for notifying a patient which are readily understood by one of ordinary skill. In certain embodiments, the state 314 can also include data storage wherein results from the measurements, calculations and comparisons of states 306, 310, 312 can be stored for use in adjustment of the programming of the device 10 and/or for other diagnostic evaluation by a clinician.

Following state 314, is a state 316 wherein, as the results of state 314 indicate that the patient is likely to be responsive to bi-ventricular pacing, the patient is provided with a device 10 having bi-ventricular pacing capability. In certain embodiments, state 316 includes providing the device 10 and patient with additional sensing and stimulation leads to provide bi-ventricular pacing which may include implanting one or more additional electrodes/leads. The device 10 is also programmed appropriately for the patient's individual condition. Thus, in certain embodiments, upon determination that the patient is likely to benefit from bi-ventricular pacing, the device 10 can be transformed from a first configuration lacking bi-ventricular pacing to a second configuration with bi-ventricular pacing. In other embodiments, the device 10 is replaced with another device 10 having the now indicated functionality.

In other embodiments, indicated as state 316', the results of state 314 indicating relatively severe contractile dysynchrony can be utilized in the state 316' to readjust the programming or configuration of the device 10 in an attempt to restore greater synchrony to the patient's heart contractions. For example, in embodiments wherein the device 10 is configured to provide bi-ventricular pacing, the reprogramming of state 316' can adjust one or more operational parameters of the device 10, such as rate parameters, AV/PV delays, VV timing etc. to provide improved delivery of therapy. In certain embodiments the reprogramming of state 316' proceeds automatically and in other embodiments, the reprogramming of state 316' is performed via active interaction of attending clinical personnel. The method 300 follows up with further measuring and evaluation as previously described fro states 304, 306, 310, 312, 314 in an ongoing iterative manner.

In this embodiment, if the comparison of state 312 indicates that the synchrony indicator $V^2$ lies between the lower threshold $T_L$ and the upper threshold $T_H$, the method proceeds to a flag state 320 wherein a flag or alert is set for subsequent follow-up. State 320 is indicative that the device 10 and method 300 have determined that the patient is in a borderline condition of not exhibiting clear contractile dysynchrony yet also not exhibiting a fully desired degree of synchrony. Thus, in certain embodiments, the state 320 corresponds to a flag or alert that is set to notify a clinician either immediately or at a subsequent follow-up clinical evaluation that the patient be further evaluated, such as for a change in the configuration of the implanted device 10 and/or a reprogramming of the device 10 and/or initiation or modification of other treatment regimens.

In one embodiment, the method 300 includes a state 322 wherein the synchronization score is stored, such as every minute, along with the associated heart rate and activity level. The state 322 provides a record or history of the patient's exhibited synchrony. This record can be communicated to a physician, such as via the external device 102. This will allow a physician or automated system to study the dependence of the synchronization on these other variables and better treat the patient.

Thus, in these embodiments, the device 10 and method 300 provide the capability to readily evaluate in an automated manner the condition of a patient provided with the device 10 and more particularly to evaluate the degree of contractile synchrony exhibited by their heart 12. This evaluation can be utilized as a clinical indicator for a more severe CHF condition as well as the likelihood that the patient would be responsive if provided with bi-ventricular pacing with appropriate programming. The device 10 and method 300 can perform this evaluation with otherwise conventional configurations for the design and implantation of the device 10 thus simplifying provision of these capabilities with reduced burden on the implanting physician.

The device 10 and method 300 can be provided with relatively inexpensive modifications to the hardware and operating software of the device 10 thus reducing the incremental cost to provide the capabilities of these embodiments. The device 10 and method 300 can also provide the ability to automatically evaluate the patient for responsiveness to bi-ventricular pacing on a periodic ongoing basis without requiring the immediate presence of a skilled clinician and relatively expensive diagnostic equipment. The method 300 and device 10 also provide the capability that these automated measurements and evaluations can be stored as well as telemetrically provided to an external device to provide the clinician with a clear indication of the potential benefit to the patient of providing the more expensive bi-ventricular pacing therapy thus simplifying and facilitating satisfying efficacy requirements of insurance companies.

Although the above disclosed embodiments of the present teachings have shown, described and pointed out the fundamental novel features of the invention as applied to the above-disclosed embodiments, it should be understood that various omissions, substitutions, and changes in the form of the detail of the devices, systems and/or methods illustrated may be made by those skilled in the art without departing from the scope of the present teachings. Consequently, the scope of the invention should not be limited to the foregoing description but should be defined by the appended claims.

What is claimed is:

1. A method of predicting a patient's response to multi-chamber pacing comprising:
   measuring across at least two spatially different impedance vectors of a patient's heart via at least three implanted electrodes to obtain at least two impedance signals; and
   evaluating the at least two impedance signals for indications of contractile dysynchrony in the heart and wherein indications of contractile dysynchrony comprise positive indicators for the patient's response to multi-chamber pacing;
   wherein measuring the at least two different impedance vectors comprises defining a different code sequence along each of the two impedance vectors, delivering a test current signal comprising the different code sequences along the two vectors, and decoding the voltage signals measured across each vector to separate out independent impedance vectors.

2. The method of claim 1, wherein evaluating the vectors comprises correlating the two impedance vectors during systole and comparing a degree of correlation to a threshold value.

3. The method of claim 1, wherein evaluating the vectors comprises correlating the two impedance vectors during diastole and comparing a degree of correlation to a threshold value.

4. The method of claim 1, wherein the at least three implanted electrodes are arranged to measure signals indicative of left ventricular contraction.

5. The method of claim 1, wherein evaluating the impedance vectors for contractile dysynchrony comprises calculating at least one product curve of at least two impedance signals and wherein dysynchrony is indicated by a reduced area under the product curve.

6. The method of claim 1, wherein, upon an indication of contractile dysynchrony in excess of a threshold value, the method further comprises generating an alert that the patient is likely to respond to bi-ventricular pacing.

7. The method of claim 6, wherein upon an indication of contractile dysynchrony of an intermediate range between threshold values, the method further comprises generating a flag for follow-up evaluation.

8. The method of claim 1, further comprising determining at least one phase difference for at least one contraction event with respect to two or more of the impedance signals and wherein contractile dysynchrony is indicated by one or more of the phase differences exceeding a threshold.

9. The method of claim 1, wherein implanting the at least three electrodes comprises implanting an implantable cardiac stimulation device such that a housing of the device is configured as one of the at least three electrodes.

10. The method of claim 1, further comprising storing a record of the indications of contractile dysynchrony.

11. The method of claim 10, further comprising storing a record of a heart rate and activity level corresponding to the indications of contractile dysynchrony such that a clinician can evaluate interdependence of the heart rate, activity level, and indications of contractile dysynchrony over time.

12. A method of predicting a patient's response to multi-chamber pacing comprising:
   measuring across at least two spatially different impedance vectors of a patient's heart via at least three implanted electrodes to obtain at least two impedance signals; and
   evaluating the at least two impedance signals for indications of contractile dysynchrony in the heart and wherein indications of contractile dysynchrony comprise positive indicators for the patient's response to multi-chamber pacing;
   wherein measuring the at least two different impedance vectors comprises defining a different frequency along each of the two impedance vectors, delivering a test current signal comprising the different frequencies multiplexed together along the two vectors, and frequency decoding the voltage signals measured across each vector to separate out independent impedance vectors.

13. The method of claim 12, wherein the at least three implanted electrodes are arranged to measure signals indicative of left ventricular contraction.

14. The method of claim 12, wherein evaluating the impedance vectors for contractile dysynchrony comprises calculating at least one product curve of at least two impedance signals and wherein dysynchrony is indicated by a reduced area under the product curve.

15. The method of claim 12, wherein, upon an indication of contractile dysynchrony in excess of a threshold value, the method further comprises generating an alert that the patient is likely to respond to bi-ventricular pacing.

16. The method of claim 15, wherein upon an indication of contractile dysynchrony of an intermediate range between threshold values, the method further comprises generating a flag for follow-up evaluation.

17. The method of claim 12, further comprising determining at least one phase difference for at least one contraction event with respect to two or more of the impedance signals and wherein contractile dysynchrony is indicated by one or more of the phase differences exceeding a threshold.

18. The method of claim 12, wherein implanting the at least three electrodes comprises implanting an implantable cardiac stimulation device such that a housing of the device is configured as one of the at least three electrodes.

19. The method of claim 12, further comprising storing a record of the indications of contractile dysynchrony.

20. The method of claim 19, further comprising storing a record of a heart rate and activity level corresponding to the indications of contractile dysynchrony such that a clinician can evaluate interdependence of the heart rate, activity level, and indications of contractile dysynchrony over time.

* * * * *